US010750945B2

(12) United States Patent
Suzuki et al.

(10) Patent No.: US 10,750,945 B2
(45) Date of Patent: Aug. 25, 2020

(54) BIOLOGICAL SIGNAL RECORDING SYSTEM

(71) Applicant: NIHON KOHDEN CORPORATION, Shinjuku-ku, Tokyo (JP)

(72) Inventors: Yoshimoto Suzuki, Tokyo (JP); Kenta Sudo, Tokyo (JP); Takayuki Kaneko, Tokyo (JP); Yoshiaki Nakao, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 540 days.

(21) Appl. No.: 15/589,082

(22) Filed: May 8, 2017

(65) Prior Publication Data
US 2017/0238802 A1 Aug. 24, 2017

Related U.S. Application Data

(63) Continuation-in-part of application No. PCT/JP2015/005666, filed on Nov. 12, 2015.

(30) Foreign Application Priority Data

Nov. 13, 2014 (JP) ................................. 2014-230944

(51) Int. Cl.
A61B 5/00 (2006.01)
G16H 40/63 (2018.01)
(Continued)

(52) U.S. Cl.
CPC .......... *A61B 5/0015* (2013.01); *A61B 5/0006* (2013.01); *A61B 5/04012* (2013.01);
(Continued)

(58) Field of Classification Search
CPC ........... A61B 5/00; A61B 5/04; A61B 5/0476; A61B 5/0006; A61B 5/0015;
(Continued)

(56) References Cited

U.S. PATENT DOCUMENTS 6,441,747 B1 8/2002 Khair et al.
6,626,676 B2 * 9/2003 Freer .................... A61B 5/0482
434/236
(Continued)

FOREIGN PATENT DOCUMENTS

CA 2097967 A1 12/1993
JP 6-7307 A 1/1994
(Continued)

OTHER PUBLICATIONS

Int. Search Report dated Feb. 29, 2016 issued in Application No. PCT/JP2015/005666 (PCT/ISA/210).
(Continued)

*Primary Examiner* — Eric J Messersmith
(74) *Attorney, Agent, or Firm* — Sughrue Mion, PLLC

(57) ABSTRACT

A transmission device can be carried by the subject. A biological signal recording device can perform wireless communication with the transmission device. A transmitter transmits biological signal data corresponding to a biological signal of a subject. A storage stores the biological signal data. A receiver receives the biological signal data. A recorder records the biological signal data received by the receiver. A detector detects a missing portion in the biological signal data recorded by the recorder or a receipt of the biological signal data by the receiver. A notifier notifies the missing portion or transmits an acknowledgment of the receipt to the transmission device. A complementary transmitter retrieves biological signal data corresponding to the notified missing portion from the storage or identifies unreceived biological signal data and retrieves the identified biological signal data, and transmits the retrieved biological signal data. A complementary recorder records the biological signal data transmitted by the complementary transmitter.

12 Claims, 4 Drawing Sheets

(51) Int. Cl.
  *A61B 5/0432* (2006.01)
  *H04L 1/16* (2006.01)
  *G06F 19/00* (2018.01)
  *A61B 5/04* (2006.01)
  *A61B 5/0476* (2006.01)
  *A61B 5/0478* (2006.01)

(52) U.S. Cl.
  CPC .......... *A61B 5/0432* (2013.01); *A61B 5/0476* (2013.01); *A61B 5/6814* (2013.01); *A61B 5/6898* (2013.01); *G06F 19/3418* (2013.01); *G16H 40/63* (2018.01); *H04L 1/16* (2013.01); *A61B 5/0478* (2013.01); *A61B 2560/0276* (2013.01)

(58) Field of Classification Search
  CPC . A61B 5/0432; A61B 5/6898; A61B 5/04012; A61B 5/6814; A61B 2560/0276; A61B 5/0478; H04L 1/16; G06F 19/3418; G16H 40/63
  See application file for complete search history.

(56) References Cited

U.S. PATENT DOCUMENTS

| | | | |
|---|---|---|---|
| 6,897,788 | B2 | 5/2005 | Khair et al. |
| RE44,487 | E | 9/2013 | Hughes et al. |
| 2002/0109621 | A1 | 8/2002 | Khair et al. |
| 2003/0169708 | A1* | 9/2003 | Harris .................. H04L 1/0001 370/335 |
| 2003/0171689 | A1 | 9/2003 | Millan et al. |
| 2005/0119535 | A1 | 6/2005 | Yanagihara et al. |
| 2008/0148131 | A1 | 6/2008 | Hughes et al. |
| 2009/0252236 | A1* | 10/2009 | Li .......................... H04B 7/061 375/260 |
| 2012/0275292 | A1* | 11/2012 | Micu .................... A61B 5/0006 370/216 |
| 2014/0362679 | A1* | 12/2014 | Yap .................... H03M 13/6306 370/216 |
| 2015/0248833 | A1 | 9/2015 | Arne et al. |

FOREIGN PATENT DOCUMENTS

| | | |
|---|---|---|
| JP | 2003-533262 A | 11/2003 |
| JP | 2004-503266 A | 2/2004 |
| JP | 2005-152401 A | 6/2005 |
| JP | 2006-191368 A | 7/2006 |
| JP | 2007-243413 A | 9/2007 |
| JP | 2007-330424 A | 12/2007 |
| JP | 2010-514264 A | 4/2010 |
| WO | 2014/047205 A1 | 3/2014 |

OTHER PUBLICATIONS

Written Opinion dated Feb. 29, 2016 issued in Application No. PCT/JP2015/005666 (PCT/ISA/237).

Communication dated Jul. 24, 2018, from the Japanese Patent Office in counterpart application No. 2014-230944.

Communication dated Mar. 6, 2018, issued by the Japanese Patent Office in counterpart Japanese application No. 2014-230944.

* cited by examiner

FIG. 2A

| TIME | STORAGE 32 | COMMNICATION STATUS | RECORDER 42 |
|---|---|---|---|
| t1 | D1 | OK | D1 |
| t2 | D1 D2 | OK | D1 D2 |
| t3 | D1 D2 D3 | OK | D1 D2 D3 |
| t4 | D1 D2 D3 D4 | OK | D1 D2 D3 D4 |
| t5 | D1 D2 D3 D4 D5 | OK | D1 D2 D3 D4 D5 |

BIOLOGICAL SIGNAL RECORDING SYSTEM

CROSS REFERENCE TO RELATED APPLICATIONS

This application is a continuation-in-part of International Patent Application No. PCT/JP2015/005666 filed on Nov. 12, 2015, claiming priority from Japanese Patent Application No. 2014-230944 filed on Nov. 13, 2014, the contents of which are incorporated herein by reference.

BACKGROUND

The presently disclosed subject matter relates to a system for recording a biological signal of a subject.

For example, JP2005-152401A discloses a system of this kind. The system includes a biological signal acquirer, a transmission device, and a biological signal recording device. The biological signal acquirer is attached to a subject to acquire a biological signal of the subject. The transmission device is carried by the subject, and transmits biological signal data corresponding to the biological signal acquired by the biological signal acquirer, to the biological signal recording device.

SUMMARY

Illustrative aspects of the present invention provide a system for transmitting biological signal data corresponding to a biological signal of a subject from a transmission device carried by the subject to a biological signal recording device, the system being configured to record the biological signal data without missing data regardless of the communication status between the transmission device and the biological signal recording device.

According to an illustrative aspect of the present invention, a biological signal recording system for recording a biological signal of a subject is provided. The biological signal recording system includes a biological signal acquirer configured to be attached to the subject, and to acquire a biological signal of the subject, a transmission device configured to be carried by the subject, and a biological signal recording device configured to perform wireless communication with the transmission device. The transmission device includes a transmitter configured to transmit biological signal data corresponding to the biological signal, and a storage configured to store biological signal data which is to be transmitted by the transmitter. The biological signal recording device includes a receiver configured to receive biological signal data which is transmitted by the transmitter, a recorder configured to record biological signal data which is received by the receiver, a detector configured to detect a missing portion in biological signal data which is recorded by the recorder, and a notifier configured to notify the missing portion which is detected by the detector to the transmission device. The transmission device includes a complementary transmitter configured to retrieve biological signal data corresponding to the missing portion which is notified by the notifier from the storage and to transmit the retrieved biological signal data. The biological signal recording device includes a complementary recorder configured to record the biological signal data corresponding to the missing portion which is transmitted by the complementary transmitter.

According to an illustrative aspect of the present invention, a biological signal recording system for recording a biological signal of a subject is provided. The biological signal recording system includes a biological signal acquirer configured to be attached to the subject, and to acquire a biological signal of the subject, a transmission device configured to be carried by the subject, and a biological signal recording device configured to perform wireless communication with the transmission device. The transmission device includes a transmitter configured to transmit biological signal data corresponding to the biological signal, and a storage configured to store biological signal data which is to be transmitted by the transmitter. The biological signal recording device includes a receiver configured to receive biological signal data which is transmitted by the transmitter, a recorder configured to record biological signal data which is received by the receiver, a detector configured to detect a receipt of biological signal data by the receiver, and a notifier configured to transmit an acknowledgment of the receipt detected by the detector to the transmission device. The transmission device includes a complementary transmitter configured to identify biological signal data not received by the receiver when the acknowledgment of the receipt is not received for a predetermined period of time, to retrieve the identified biological signal data from the storage and to transmit the retrieved biological signal data. The biological signal recording device includes a complementary recorder configured to record the biological signal data which is transmitted by the complementary transmitter.

Other aspects and advantages of the invention will be apparent from the following description, the drawings and the claims.

BRIEF DESCRIPTION OF DRAWINGS

FIG. 2A is a diagram for explaining operations of the system;

DETAILED DESCRIPTION

Figure 1:
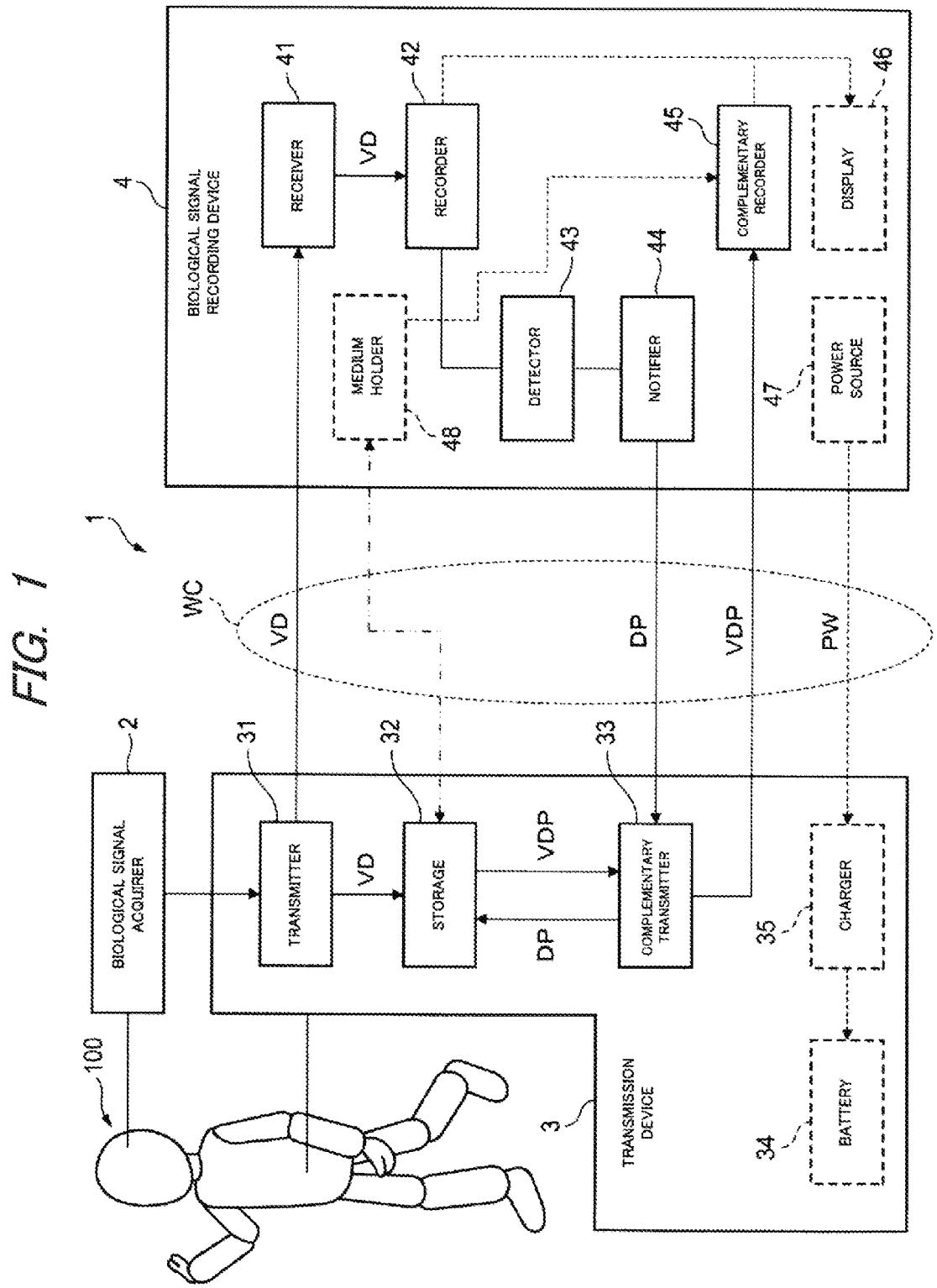
FIG. 1 is a diagram showing a configuration of a biological signal recording system according to one embodiment.

An example embodiment of the invention will be described in detail with reference to the accompanying drawings. FIG. 1 is a functional block diagram showing a biological signal recording system 1 according to one embodiment.

The biological signal recording system 1 is a system which acquires biological information of a subject 100. The biological signal recording system 1 includes a biological signal acquirer 2. The biological signal acquirer 2 is configured to be attached to a subject 100, and to acquire a biological signal of the subject 100. The biological signal acquirer 2 is constituted by, for example, a plurality of electrodes which are to be attached to the head of the subject 100. The biological signal is, for example, the brain wave.

The biological signal recording system 1 includes a transmission device 3. The transmission device 3 is a device configured to be portably carried by the subject 100. Namely, the biological signal acquirer 2 and the transmission device 3 are moved together with the subject 100. The transmission device 3 is configured to receive a biological signal acquired by the biological signal acquirer 2. That is, the biological signal acquirer 2 and the transmission device 3 are configured to perform wired or wireless communication.

The biological signal recording system 1 includes a biological signal recording device 4. The biological signal recording device 4 is configured to perform wireless communication with the transmission device 3. For example the biological signal recording device 4 is an electroencephalograph.

The transmission device 3 includes a transmitter 31. The transmitter 31 is configured to transmit biological signal data VD corresponding to a biological signal of the subject 100 which is acquired by the biological signal acquirer 2, to the biological signal recording device 4.

The transmission device 3 includes a storage 32. The storage 32 is configured to store the biological signal data VD transmitted from the transmitter 31. The storage 32 is configured to store the biological signal data VD regardless of the communication status between the transmission device 3 and the biological signal recording device 4.

The biological signal recording device 4 includes a receiver 41. The receiver 41 is configured to receive the biological signal data VD transmitted from the transmitter 31 of the transmission device 3.

The biological signal recording device 4 includes a recorder 42. The recorder 42 is configured to record the biological signal data VD received by the receiver 41.

The biological signal recording device 4 includes a detector 43. The detector 43 is configured to detect a missing portion DP of the biological signal data VD recorded in the recorder 42.

The biological signal recording device 4 includes a notifier 44. The notifier 44 is configured to notify the transmission device 3 of the missing portion DP of the biological signal data VD which is detected by the detector 43.

The transmission device 3 includes a complementary transmitter 33. The complementary transmitter 33 is configured to retrieved biological signal data VDP corresponding to the missing portion DP which is notified by the notifier 44 of the biological signal recording device 4, from the storage 32. The complementary transmitter 33 is further configured to transmit the biological signal data VDP which are retrieved from the storage 32, to the biological signal recording device 4.

The biological signal recording device 4 includes a complementary recorder 45. The complementary recorder 45 is configured to record the biological signal data VDP which are transmitted from the complementary transmitter 33 of the transmission device 3. Although not illustrated in FIG. 1, the biological signal data VDP which are transmitted from the complementary transmitter 33 are received by the receiver 41, and then recorded in the complementary recorder 45.

Figure 2B:
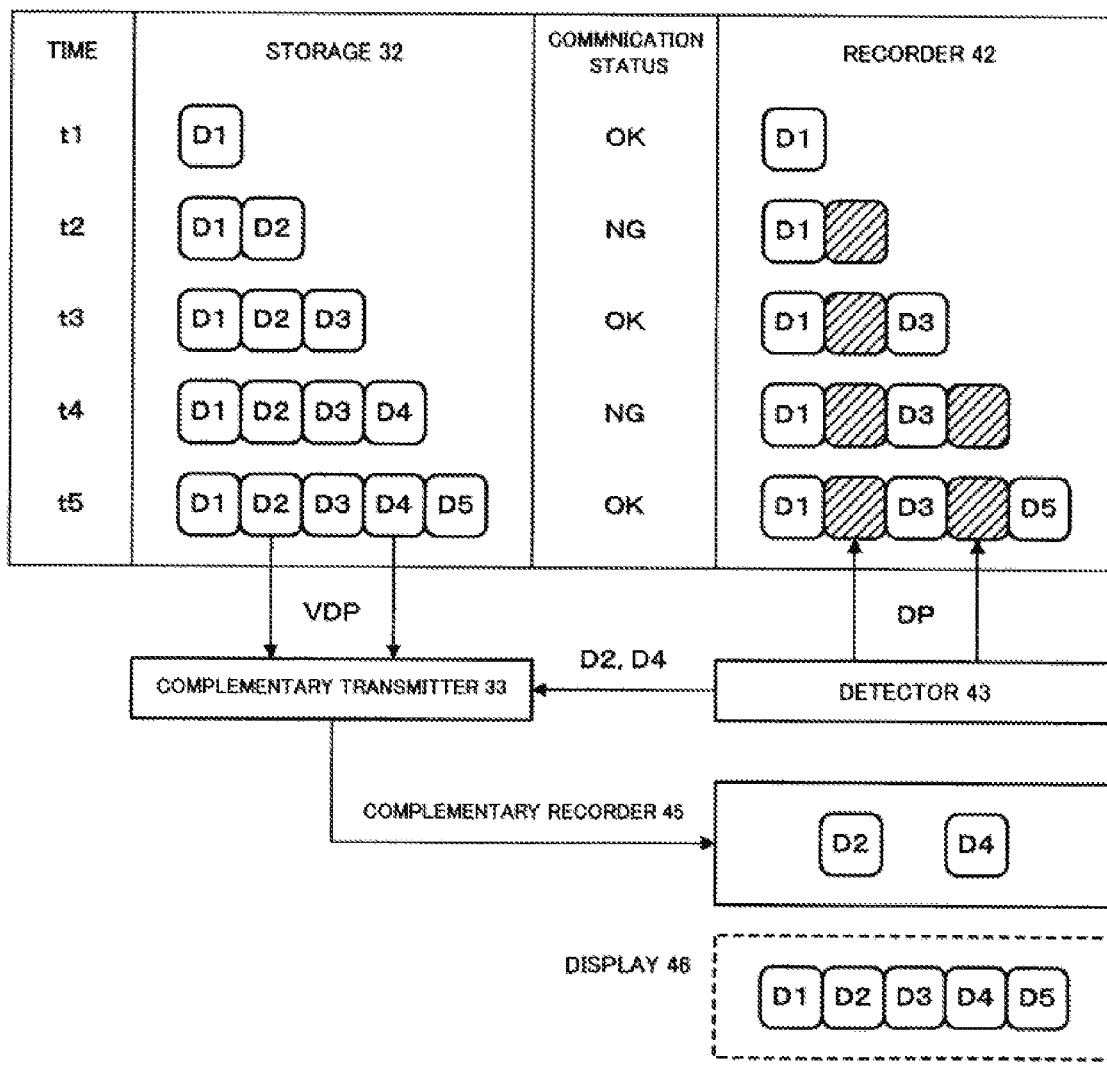
FIG. 2B is a diagram for explaining operations of the system.

The operation of the thus configured biological signal recording system 1 will be described with reference to FIGS. 2A and 2B. FIG. 2A shows a state where communication between the transmission device 3 and the biological signal recording device 4 continues to be valid. FIG. 2B shows a state where communication between the transmission device 3 and the biological signal recording device 4 is invalid temporarily.

In the following description, biological signal data VD corresponding to a biological signal which is acquired at time t1 by the biological signal acquirer 2 is indicated by the reference numeral D1. Similarly, biological signal data VD corresponding to biological signals which are acquired at times t2, t3, t4, and t5 by the biological signal acquirer 2 are indicated by the reference numerals D2, D3, D4, and D5, respectively. In this description, the term "time t1" means a time period of a certain length including a time point t1. This is similarly applicable also to times t2 to t5.

The biological signal data D1 corresponding to the biological signal of the certain length which is acquired at time t1 by the biological signal acquirer 2 is supplied to the transmission device 3. As shown in FIG. 2A, the storage 32 of the transmission device 3 stores the biological signal data D1. On the other hand, the transmitter 31 of the transmission device 3 transmits the biological signal data D1 to the biological signal recording device 4. The communication between the transmission device 3 and the biological signal recording device 4 is established at time t1, and therefore the receiver 41 of the biological signal recording device 4 can receive the biological signal data D1. The recorder 42 of the biological signal recording device 4 records the received biological signal data D1 in real time.

The biological signal data D2 corresponding to the biological signal of the certain length which is acquired at time t2 by the biological signal acquirer 2 is supplied to the transmission device 3. As shown in FIG. 2A, the storage 32 of the transmission device 3 stores the biological signal data D2. On the other hand, the transmitter 31 of the transmission device 3 transmits the biological signal data D2 to the biological signal recording device 4. The communication between the transmission device 3 and the biological signal recording device 4 is established at time t2, and therefore the receiver 41 of the biological signal recording device 4 can receive the biological signal data D2. The recorder 42 of the biological signal recording device 4 records the received biological signal data D2 in real time. Therefore, each of the storage 32 and the recorder 42 holds the biological signal data D1 and D2.

A similar process is performed also at times t3 to t5. Since the communication between the transmission device 3 and the biological signal recording device 4 continues to be valid, each of the storage 32 and the recorder 42 holds the biological signal data D1 to D5 at time t5.

Next, referring to FIG. 2B, the case where the communication between the transmission device 3 and the biological signal recording device 4 is disrupted at time t2 will be described. Examples of the cause of disruption of the communication are a change of the status of the wireless communication due to movement of the subject 100, and reduction of the data transmission capability of the transmitter 31 due to reduction of the remaining charge of the battery for driving the transmission device 3.

The operation at time t1 is identical with that in the case of FIG. 2A.

The biological signal data D2 corresponding to the biological signal of the certain length which is acquired at time t2 by the biological signal acquirer 2 is supplied to the transmission device 3. The storage 32 of the transmission device 3 stores the biological signal data D2. On the other hand, the transmitter 31 of the transmission device 3 transmits the biological signal data D2 to the biological signal recording device 4. At time t2, however, the communication between the transmission device 3 and the biological signal recording device 4 is disrupted, and therefore the receiver 41 of the biological signal recording device 4 cannot receive the biological signal data D2. Therefore, the storage 32 holds the biological signal data D1 and D2, but the recorder 42 holds only the biological signal data D1.

The biological signal data D3 corresponding to the biological signal of the certain length which is acquired at time t3 by the biological signal acquirer 2 is supplied to the transmission device 3. The storage 32 of the transmission device 3 stores the biological signal data D3. On the other hand, the transmitter 31 of the transmission device 3 transmits the biological signal data D3 to the biological signal recording device 4. At time t3, the communication between the transmission device 3 and the biological signal recording device 4 is established, and therefore the receiver 41 of the biological signal recording device 4 can receive the biological signal data D3. The recorder 42 of the biological signal recording device 4 records the received biological signal data D3 in real time. Therefore, the storage 32 holds the biological signal data D1 to D3, but the recorder 42 holds only the biological signal data D1 and D3.

The biological signal data D4 corresponding to the biological signal of the certain length which is acquired at time t4 by the biological signal acquirer 2 is supplied to the transmission device 3. The storage 32 of the transmission device 3 stores the biological signal data D4. On the other hand, the transmitter 31 of the transmission device 3 transmits the biological signal data D4 to the biological signal recording device 4. At time t4, however, the communication between the transmission device 3 and the biological signal recording device 4 is disrupted, and therefore the receiver 41 of the biological signal recording device 4 cannot receive the biological signal data D4. Therefore, the storage 32 holds the biological signal data D1 to D4, but the recorder 42 holds only the biological signal data D1 and D3.

The biological signal data D5 corresponding to the biological signal of the certain length which is acquired at time t5 by the biological signal acquirer 2 is supplied to the transmission device 3. The storage 32 of the transmission device 3 stores the biological signal data D5. On the other hand, the transmitter 31 of the transmission device 3 transmits the biological signal data D5 to the biological signal recording device 4. At time t5, the communication between the transmission device 3 and the biological signal recording device 4 is established, and therefore the receiver 41 of the biological signal recording device 4 can receive the biological signal data D5. The recorder 42 of the biological signal recording device 4 records the received biological signal data D5 in real time. Therefore, the storage 32 holds the biological signal data D1 to D5, but the recorder 42 holds only the biological signal data D1, D3, and D5.

The detector 43 of the biological signal recording device 4 detects the absence of the biological signal data D2 and D4 in the recorder 42, as the missing portion DP of the biological signal data. The notifier 44 notifies the transmission device 3 of the detected missing portion DP. The notification by the notifier 44 is performed in a manner that the missing portion DP can be recognized as the biological signal data D2 and D4, during a period when the communication between the transmission device 3 and the biological signal recording device 4 is established.

The complementary transmitter 33 of the transmission device 3 retrieves the biological signal data VDP corresponding to the missing portion DP of the biological signal data which is notified by the detector 43, from the storage 32. Here, the biological signal data D2 and D4 correspond to the biological signal data VDP. During a period when the communication between the transmission device 3 and the biological signal recording device 4 is established, the complementary transmitter 33 transmits the retrieved biological signal data D2 and D4 to the biological signal recording device 4. The receiver 41 of the biological signal recording device 4 receives the biological signal data D2 and D4 transmitted from complementary transmitter 33. The complementary recorder 45 of the biological signal recording device 4 records the biological signal data D2 and D4 received by the receiver 41.

According to the configuration, regardless of the communication status between the transmission device 3 and the biological signal recording device 4, all of the biological signal data VD (D1 to D5) corresponding to the biological signal of the subject 100 which is acquired by the biological signal acquirer 2 are stored in the storage 32 of the transmission device 3. When the communication between the transmission device 3 and the biological signal recording device 4 is recovered from the disruption status, the biological signal data VD which are received by the receiver 41 of the biological signal recording device 4 are recorded in the recorder 42 of the biological signal recording device 4 regardless of presence of the biological signal data VD (D2, D4) which could not be received during the communication disruption. The presence of the biological signal data which could not be received during the communication disruption, or in other words presence of the missing portion DP (D2, D4) of the biological signal data is detected by the detector 43 of the biological signal recording device 4, and then notified to the transmission device 3 by the notifier 44 of the biological signal recording device 4. The complementary transmitter 33 of the transmission device 3 retrieves the biological signal data VDP (D2, D4) corresponding to the notified missing portion DP from the storage 32, and transmits the data to the biological signal recording device 4. The biological signal data VDP transmitted by the complementary transmitter 33 are recorded in the complementary recorder 45 of the biological signal recording device 4. Finally, therefore, all of the biological signal data VD corresponding to the biological signal of the subject 100 which is acquired by the biological signal acquirer 2 are stored in the biological signal recording device 4.

Namely, when the communication between the transmission device 3 and the biological signal recording device 4 is recovered from the disruption status, the real time recording of the received biological signal data VD is given preference in the biological signal recording device 4. The biological signal data VDP corresponding to the missing portion DP of the biological signal data which could not be received during the communication disruption are complementarily recorded in the biological signal recording device 4 in response to ex-post notification to the transmission device 3. In the system which transmits the biological signal data VI) corresponding to the biological signal of the subject 100 from the transmission device 3 carried by the subject 100 to the biological signal recording device 4, therefore, the biological signal data VD can be recorded without missing data regardless of the communication status between the transmission device 3 and the biological signal recording device 4. According to the thus configured system, moreover, it is not necessary to constrain the subject 100 in a fixed place in order to maintain the communication establishment status between the transmission device 3 and the biological signal recording device 4. Therefore, a burden on the subject 100 can be suppressed even in the case where the recording of a biological signal is performed for a long period of time.

The timing when the detector 43 of the biological signal recording device 4 detects the missing portion DP of biological signal data may be adequately determined. For example, the detector 43 may detect that portion each time when the missing portion DP is established (in the example shown in FIG. 2B, time t3 and time t5). Alternatively, the detector 43 may collectively detect all missing portions DP after recording of the biological signal in a certain unit is finished.

The timing when the notifier 44 of the biological signal recording device 4 notifies the transmission device 3 of the missing portion DP of biological signal data to may be adequately determined. For example, the notifier 44 may perform the notification each time when the detector 43 detects the missing portion DP. Alternatively, the notifier 44 may perform the notification each time a predetermined number of missing portions DP have been detected. Alternatively, the notifier 44 may collectively notify all missing portions DP after recording of the biological signal in a certain unit is finished.

The storage 32 of the transmission device 3 may be configured so that, each time the biological signal data VDP corresponding to the missing portion DP is retrieved by the complementary transmitter 33, the biological signal data VD which have been stored temporally earlier than the retrieved biological signal data are deleted. This is performed because it is established that such biological signal data VD have been already stored in the biological signal recording device 4. In the case of the example shown in FIG. 2B, the biological signal data D1 and D3 may be deleted after the biological signal data D2 and D4 are retrieved. Since the transmission device 3 has the configuration in which it is carried by the subject 100, it is relatively difficult to ensure a large storage capacity in the storage 32. According to the above-described configuration, particularly in the case where the capacity of the storage 32 is relatively small, it is possible to save the storage area.

In this embodiment, the storage 32 of the transmission device 3 is configured to store the biological signal data VD in association with time information. The time information is produced by an internal tinier which is disposed in the transmission device 3, and which is not shown. On the other hand, the recorder 42 of the biological signal recording device 4 is configured to record the biological signal data VD received by the receiver 41, in association with time information. The time information is produced by an internal timer which is disposed in the biological signal recording device 4, and which is not shown. The internal timers of the transmission device 3 and the biological signal recording device 4 are synchronized with each other.

In this case, the missing portion DP of the biological signal data is associated with time information which is during the disruption status of the communication between the transmission device 3 and the biological signal recording device 4. The notifier 44 of the biological signal recording device 4 is configured to notify the transmission device 3 of the time information associated with the missing portion DP of the biological signal data detected by the detector 43. On the other hand, the complementary transmitter 33 of the transmission device 3 is configured to retrieve the biological signal data VDP associated with the time information corresponding to the time information notified by the notifier 44, from the storage 32.

According to the configuration, the missing portion DP of the biological signal data in the recorder 42 of the biological signal recording device 4 can be easily associated with the biological signal data VDP corresponding to the missing portion in the storage 32 of the transmission device 3. Therefore, the missing portion DP of the biological signal data in the biological signal recording device 4 is easily complemented. In the system which transmits the biological signal data VD corresponding to the biological signal of the subject 100 from the transmission device 3 carried by the subject 100 to the biological signal recording device 4, therefore, the biological signal data VD can be easily recorded without missing data regardless of the communication status between the transmission device 3 and the biological signal recording device 4.

In the case where the missing portion DP of the biological signal data in the recorder 42 of the biological signal recording device 4 can be associated with the biological signal data VDP corresponding to the missing portion in the storage 32 of the transmission device 3, the reference Which is used in the associating process is not limited to time information. For example, the addresses of the storage areas of the storage 32 and the recorder 42, or a reference number which is provided to biological signal data may be used as the reference.

As indicated by the dashed lines in FIG. 1, the biological signal recording device 4 includes a display 46. The display 46 is configured to display, in chronological order, the biological signal data VD recorded in the recorder 42 and the biological signal data VDP recorded in the complementary recorder 45. In the case of the example shown in FIG. 2B, the biological signal data D1, D3, and D5 are stored in the recorder 42, and the biological signal data D2 and D4 are stored in the complementary recorder 45. Therefore, the display 46 displays the biological signal data in the sequence of D1, D2, D3, D4, and D5.

According to the configuration, the display can be performed as if the biological signal of the subject 100 continues to be recorded in real time, regardless of the history of the communication status between the transmission device 3 and the biological signal recording device 4. In the system which transmits the biological signal data VD corresponding to the biological signal of the subject 100 from the transmission device 3 carried by the subject 100 to the biological signal recording device 4, therefore, the biological signal data VD can be recorded without missing data regardless of the communication status between the transmission device 3 and the biological signal recording device 4, and moreover the biological signal can be displayed as if no missing data exist.

As indicated by the dashed lines in FIG. 1, the biological signal recording device 4 includes a power supply 47. The power supply 47 is configured to acquire an electric power from a commercial power supply, and supply the power to various sections of the biological signal recording device 4. On the other hand, the transmission device 3 includes a battery 34. The battery 34 is configured to supply an electric power stored in the battery itself to various sections of the transmission device 3.

As indicated by the dashed lines in FIG. 1, the transmission device 3 and the biological signal recording device 4 can be configured to be communicable with each other through a wired connection WC. In this case, the transmission device 3 can include a charger 35. The charger 35 is configured to charge the battery 34 with an electric power PW which is supplied from the power supply 47 of the biological signal recording device 4 through the wired connection WC.

As described above, reduction of the remaining charge of the battery 34 may cause disruption of the wireless communication between the transmission device 3 and the biological signal recording device 4. According to the configuration, however, the battery 34 can be charged by taking the opportunity to perform communication between the transmission device 3 and the biological signal recording device 4 through the wired connection WC. Therefore, the time period when the valid status of communication between the transmission device 3 and the biological signal recording device 4 is maintained can be prolonged. In the system which transmits the biological signal data VD corresponding to the biological signal of the subject 100 from the transmission device 3 carried by the subject 100 to the biological signal recording device 4, consequently, the biological signal data VD can be easily recorded without missing data.

In the case where the transmission device 3 and the biological signal recording device 4 are configured to be communicable with each other through the wired connection WC, the complementary transmitter 33 of the transmission device 3 and the notifier 44 as well as complementary recorder 45 of the biological signal recording device 4 may be configured to operate when the wired connection WC is established.

According to the configuration, the reliability of data communication can be improved as compared to the case where data communication related to the notification of the missing portion DP of the biological signal data, and completion of the biological signal data VDP corresponding to the missing portion is performed through wireless communication. In the system which transmits the biological signal data VD corresponding to the biological signal of the subject 100 from the transmission device 3 carried by the subject 100 to the biological signal recording device 4, consequently, the biological signal data VD can be easily recorded without missing data.

The storage 32 of the transmission device 3 may be configured as a portable storage medium. In this case, as indicated by the dashed lines in FIG. 1, the biological signal recording device 4 may include a medium holder 48. As indicated by the dashed chain lines in FIG. 1, the medium holder 48 is configured such that the storage 32 which is a portable storage medium is detachable attached thereto. As indicated by the dashed lines in FIG. 1, the complementary recorder 45 of the biological signal recording device 4 is configured so that, when the storage 32 which is a portable storage medium is attached to the medium holder 48, the complementary recorder retrieves the biological signal data VDP corresponding to the missing portion DP of the biological signal data detected by the detector 43 of the biological signal recording device 4, from the storage 32, and records the data.

According to the configuration, the reliability of data communication can be improved as compared to the case where data communication related to the notification of the missing portion DP the biological signal data, and completion of the biological signal data VDP corresponding to the missing portion is performed through wireless communication. In the system which transmits the biological signal data VD corresponding to the biological signal of the subject 100 from the transmission device 3 carried by the subject 100 to the biological signal recording device 4, consequently, the biological signal data VD can be easily recorded without missing data.

Figure 3:
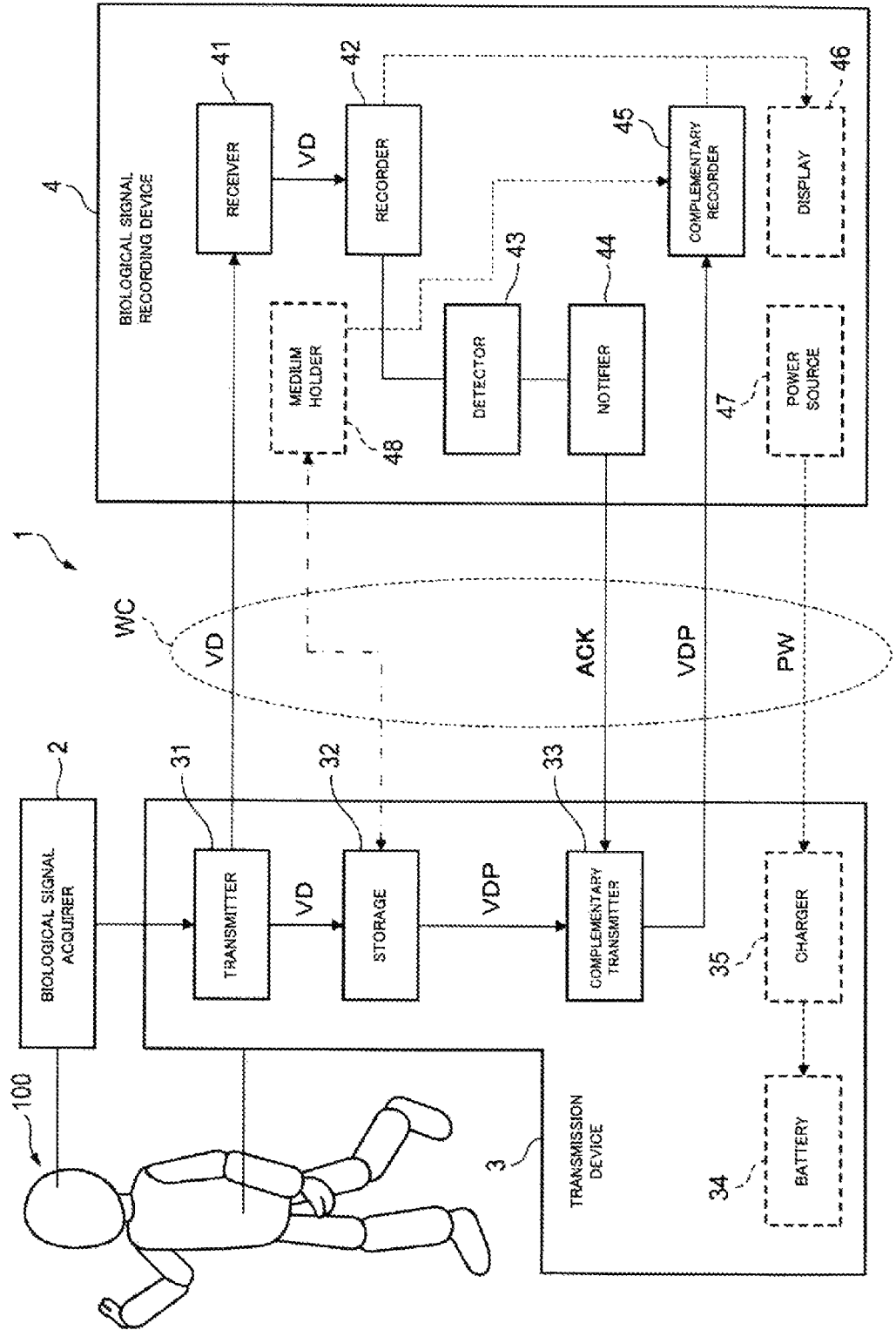
FIG. 3 is a diagram showing a configuration of a biological signal recording system according to another embodiment.

FIG. 3 illustrates a configuration of a biological signal recording system 1 according to another embodiment of the present invention. This embodiment is different from the foregoing embodiment in that the detector 43 of the biological signal recording device 4 is configured to detect, not the missing portion DP in biological signal data VD, but a receipt of the biological signal data VD transmitted from the transmission device 3, in that the notifier 44 of the biological signal recording device 4 transmits an acknowledgment ACK of the receipt detected by the detector 43 to the transmission device 3 instead of notifying the missing portion DP to the transmission device 3, and in that the complementary transmitter 33 of the transmission device 3 is configured to identify biological signal data VDP not received by the receiver 41 when the acknowledgment ACK of the receipt is not received for a predetermined period of time, to retrieve the identified biological signal data VDP from the storage 32 and to transmit the retrieved biological signal data VDP to the complementary recorder 45 of the biological signal recording device 4. Other features of the embodiment of FIG. 3 is the same or similar to those of the embodiment of FIG. 1.

The detector 43 may detect the receipt of the biological signal data VD when the receiver 41 has successfully received the biological signal data VD from the transmission device 3. The detector 43 may detect the receipt of the biological signal data VD based on the biological signal data VD recorded in the recorder 42 as illustrated in FIG. 3, or may detect the receipt of the biological signal data VD directly front the receiver 41 without reference to the recorder 42.

The transmission device 3 may be configured to withhold transmitting subsequent biological signal data until the acknowledgment ACK of the receipt is received. The transmission device 3 may be configured to store the biological signal data VD in the storage 32 when the acknowledgment ACK of the receipt is not received for the predetermined period of time.

The foregoing description of the embodiments has been made in order to facilitate understanding of the invention, and is not intended to limit the invention. It is a matter of course that the invention may be changed or modified without departing the spirit thereof, and includes equivalents thereof.

In the above embodiment, the charger 35 of the transmission device 3 is configured to charge the battery 34 with the electric power PW which is supplied from the power supply 47 of the biological signal recording device 4 through the wired connection WC. Alternatively, the charger 35 may be configured to charge the battery 34 with an electric power which is not supplied through the wired connection WC with the biological signal recording device 4, but supplied from a commercial power supply through an AC adaptor.

In the above embodiment, the example in which the biological signal acquirer 2 acquires the brain wave while the biological signal recording device 4 is an electroencephalograph has been described. In the case of an epilepsy patient, particularly, the brain wave must be continuously recorded for a long period of time in order to record a seizure. According to the configuration of the above embodiment, therefore, the brain wave can be continuously recorded while allowing the epilepsy patient to freely move. Therefore, brain wave data can be recorded without missing data while reducing the burden on the epilepsy patient. However, the invention can be applied to an arbitrary biological signal which is requested to be continuously recorded for a long period of time.

Each of the transmitter 31, storage 32, and complementary transmitter 33 of the transmission device 3 is a functional block which is realized by at least one of hardware (e.g., at least one processor and a memory) and software. In FIG. 1, the functional blocks are independent from one another. Alternatively, at least one of the blocks may be realized by a common hardware module or software module.

Each of the receiver 41, recorder 42, detector 43, notifier 44, and complementary recorder 45 of the biological signal recording device 4 is a functional block which is realized by at least one of hardware (e.g., at least one processor and a memory) and software. In FIG. 1, the functional blocks are independent from one another. Alternatively, at least one of the blocks may be realized by a common hardware module or software module.

What is claimed is:

1. A biological signal recording system for recording a biological signal of a subject is provided, the biological signal recording system comprising:
a biological signal acquirer configured to be attached to the subject, and to acquire a biological signal of the subject;
a transmission device configured to be carried by the subject; and
a biological signal recording device configured to perform wireless communication with the transmission device,
wherein the transmission device comprises:
a transmitter configured to transmit biological signal data corresponding to the biological signal, to the biological signal recording device;
a storage configured to store the biological signal data acquired by the biological signal acquirer; and
a complementary transmitter configured to identify biological signal data not received by the biological signal recording device when acknowledgment of receipt of the biological signal data from the biological signal recording device is not received for a predetermined period of time, retrieve the biological signal data not received by the biological signal recording device from the storage, and retransmit the biological signal data not received by the biological signal recording device to the biological signal recording device,
wherein the biological signal recording device comprises:
a receiver configured to receive the biological signal data from the transmitter;
a recorder configured to record the biological signal data;
a detector configured to detect the receipt of the biological signal data; and
a notifier configured to transmit an acknowledgment of the receipt of the biological signal data to the transmission device; and
a complementary recorder configured to record the biological signal data which is retransmitted by the complementary transmitter,
wherein in response to recovering the wireless communication from disruption of the wireless communication between the transmission device and the biological signal recording device, the transmitter transmits the biological signal data corresponding to the biological signal to the receiver of the biological signal recording device while the complimentary transmitter retransmits the biological signal data not received by the biological signal recording device to the complementary recorder of the biological signal recording device,
wherein the transmission device is configured to withhold transmitting subsequent biological signal data until the acknowledgment of the receipt is received.

2. A biological signal recording system for recording a biological signal of a subject is provided, the biological signal recording system comprising:
a biological signal acquirer configured to be attached to the subject, and to acquire a biological signal of the subject;
a transmission device configured to be carried by the subject; and
a biological signal recording device configured to perform wireless communication with the transmission device,
wherein the transmission device comprises:
a transmitter configured to transmit biological signal data corresponding to the biological signal, to the biological signal recording device;
a storage configured to store the biological signal data acquired by the biological signal acquirer; and
a complementary transmitter configured to identify biological signal data not received by the biological signal recording device when acknowledgment of receipt of the biological signal data from the biological signal recording device is not received for a predetermined period of time, retrieve the biological signal data not received by the biological signal recording device from the storage, and retransmit the biological signal data not received by the biological signal recording device to the biological signal recording device,
wherein the biological signal recording device comprises:
a receiver configured to receive the biological signal data from the transmitter;
a recorder configured to record the biological signal data;
a detector configured to detect the receipt of the biological signal data; and
a notifier configured to transmit an acknowledgment of the receipt of the biological signal data to the transmission device; and
a complementary recorder configured to record the biological signal data which is retransmitted by the complementary transmitter,
wherein in response to recovering the wireless communication from disruption of the wireless communication between the transmission device and the biological signal recording device, the transmitter transmits the biological signal data corresponding to the biological signal to the receiver of the biological signal recording device while the complimentary transmitter retransmits the biological signal data not received by the biological signal recording device to the complementary recorder of the biological signal recording device, wherein the transmission device is configured to store the biological signal data in the storage when the acknowledgment of the receipt is not received for the predetermined period of time.

3. The biological signal recording system as set forth in claim 1, wherein the storage is configured to store biological signal data in association with time information,
wherein the recorder is configured to record biological signal data received by the receiver in association with the time information,
wherein the notifier is configured to notify the transmission device of the missing biological signal data based on the time information, and wherein the complementary transmitter is configured to retrieve the missing biological signal data from the storage based on the time information.

4. The biological signal recording system as set forth in claim 3, wherein the biological signal recording device comprises a display configured to display in chronological order the biological signal data recorded in the recorder and the biological signal data recorded in the complementary recorder, based on the time information.

5. The biological signal recording system as set forth in claim 1, wherein the transmission device comprises:
a battery; and
a charger configured to charge the battery with externally supplied power.

6. The biological signal recording system as set forth in claim 5, wherein the transmission device and the biological signal recording device are configured to perform communication via a wire connection, and wherein the charger is configured to charge the battery with power supplied from the biological signal recording device via the wire connection.

7. The biological signal recording system as set forth in claim 1, wherein the biological signal includes brain waves, and wherein the biological signal recording device is an electroencephalograph.

8. The biological signal recording system as set forth in claim 2, wherein the storage is configured to store biological signal data in association with time information, wherein the recorder is configured to record biological signal data received by the receiver in association with the time information, wherein the notifier is configured to notify the transmission device of the missing biological signal data based on the time information, and wherein the complementary transmitter is configured to retrieve the missing biological signal data from the storage based on the time information.

9. The biological signal recording system as set forth in claim 8, wherein the biological signal recording device comprises a display configured to display in chronological order the biological signal data recorded in the recorder and the biological signal data recorded in the complementary recorder, based on the time information.

10. The biological signal recording system as set forth in claim 2, wherein the transmission device comprises:

a battery; and a charger configured to charge the battery with externally supplied power.

11. The biological signal recording system as set forth in claim 10, wherein the transmission device and the biological signal recording device are configured to perform communication via a wire connection, and wherein the charger is configured to charge the battery with power supplied from the biological signal recording device via the wire connection.

12. The biological signal recording system as set forth in claim 2, wherein the biological signal includes brain waves, and wherein the biological signal recording device is an electroencephalograph.

* * * * *